United States Patent [19]

Minaskanian

[11] Patent Number: 4,849,436
[45] Date of Patent: Jul. 18, 1989

[54] 1,4-DIHYDROPYRIDINES

[75] Inventor: Gevork Minaskanian, Irvine, Calif.

[73] Assignee: Nelson Research & Development Co., Irvine, Calif.

[21] Appl. No.: 838,536

[22] Filed: Mar. 11, 1986

[51] Int. Cl.$^4$ .................. C07D 211/86; A61K 31/455
[52] U.S. Cl. .................................... 514/356; 514/339; 514/343; 546/321; 546/273; 546/281
[58] Field of Search ....................... 546/273, 281, 321; 514/339, 343, 356

[56] References Cited

U.S. PATENT DOCUMENTS

| | | | |
|---|---|---|---|
| 3,325,505 | 6/1967 | Loev | 546/321 |
| 3,441,648 | 4/1969 | Loev et al. | 546/321 |
| 3,455,945 | 7/1969 | Loev | 546/321 |
| 3,470,297 | 9/1969 | Bossert et al. | 546/321 |
| 3,485,847 | 12/1969 | Bossert et al. | 546/321 |
| 3,488,359 | 1/1970 | Bossert et al. | 546/321 |
| 3,511,837 | 5/1970 | Bossert et al. | 546/319 |
| 3,511,847 | 5/1970 | Loev et al. | 546/321 |
| 3,644,627 | 2/1972 | Bossert et al. | 546/321 |
| 3,691,177 | 9/1972 | Bossert et al. | 546/321 |
| 3,905,970 | 9/1975 | Bossert et al. | 546/321 |
| 3,985,758 | 10/1976 | Murakami et al. | 546/321 |
| 4,145,432 | 3/1979 | Sato | 546/113 |
| 4,177,278 | 12/1979 | Bossert et al. | 546/321 |
| 4,188,395 | 2/1980 | Bossert et al. | 546/321 |
| 4,258,042 | 3/1981 | Loev et al. | 544/128 |
| 4,284,634 | 8/1981 | Satu | 546/322 |
| 4,307,103 | 12/1981 | Sato | 546/272 |
| 4,338,322 | 7/1982 | Sato | 546/321 |
| 4,348,395 | 9/1982 | Franckowiak et al. | 544/238 |
| 4,360,520 | 11/1982 | Meyer et al. | 544/224 |
| 4,370,334 | 1/1983 | Sato | 544/238 |
| 4,393,070 | 5/1983 | Sato et al. | 546/321 |
| 4,430,333 | 2/1984 | Campbell et al. | 546/321 |
| 4,446,325 | 5/1984 | Ohno et al. | 546/321 |
| 4,448,964 | 5/1984 | Muto et al. | 546/194 |
| 4,450,165 | 5/1984 | Araki et al. | 546/263 |
| 4,478,834 | 10/1984 | Shroff et al. | 546/80 |
| 4,483,985 | 11/1984 | Wehinger et al. | 544/365 |
| 4,485,239 | 11/1984 | Biseniex et al. | 546/321 |
| 4,487,932 | 12/1984 | Biseniex et al. | 546/321 |
| 4,491,581 | 1/1985 | Vogel | 544/238 |
| 4,491,582 | 1/1985 | Loev et al. | 544/238 |
| 4,492,703 | 1/1985 | Goldmann et al. | 546/321 |
| 4,495,192 | 1/1985 | Muto et al. | 514/318 |
| 4,495,356 | 1/1985 | Inoue et al. | 546/268 |
| 4,497,808 | 2/1985 | Zimmermann et al. | 514/222 |
| 4,500,527 | 2/1985 | Loev et al. | 514/223 |
| 4,500,528 | 2/1985 | Loev et al. | 514/233 |
| 4,500,532 | 2/1985 | Loev et al. | 514/256 |
| 4,503,223 | 3/1985 | Reilly, Jr. | 544/122 |
| 4,505,920 | 3/1985 | Loev et al. | 514/341 |
| 4,508,719 | 4/1985 | Tricerri et al. | 514/236 |
| 4,520,131 | 5/1985 | Loev et al. | 514/156 |
| 4,532,248 | 7/1985 | Franckowiak et al. | 514/302 |
| 4,568,677 | 2/1986 | Alker et al. | 514/272 |
| 4,622,332 | 11/1986 | Wehinger et al. | 546/321 |
| 4,652,573 | 3/1987 | Minaskanian et al. | 514/339 |
| 4,732,985 | 3/1988 | Alker et al. | 546/268 |

FOREIGN PATENT DOCUMENTS 0151006 8/1985 European Pat. Off.

OTHER PUBLICATIONS

Wolfe, S. et al. Canadian Journal of Chemistry, vol. 48 (1970) pp. 3572-3579.
Ferry, D. R. et al. FEBS Letters 169 (1) pp. 112-118 (1984).
Janis, et al., "New Developments in $Ca^{2+}$ Channel Antagonists", J. Med. Chem. 26(6), 762-769 (1983).
Thayer, et al., "An Antibody to Dihydropyridine Calcium Entry Blockers," Biochemical Pharmacology 35(24), 4479-4485 (1986).
Bossert, et al., "4-Aryldihydropyridines, A New Class of Highly Active Calcium Antagonists," Angew. Chem. Int. Ed. Engl. 20, 762-769 (1981).
Hogestatt, et al., "Effects of Nifedipine on Potassium-Induced Contraction and Noradrenaline Release in Cerebral and Extracranial Arteries from Rabbit," Acta Physiol Scand 114:283-296 (1982).
Meyer, H., et al., Chapter 9, "Calcium Antagonists—New Opportunities," Annual Rpts. Med. Chem. 18, 79-88 (1983).
Schramm, M., et al., "Novel Dihydropyridines with Positive Inotropic Action Through Activation of $Ca^{2+}$ Channels," Nature 303, 535-537 (1983).

Primary Examiner—Jane T. Fan
Attorney, Agent, or Firm—Robert J. Baran; June M. Bostich

[57] ABSTRACT

This invention provides compounds useful for treating coronary insufficiency, hypertension, angina pectoris, cardiac arrythmia, heart attack or coronary vasospasm and represented by the general formula:

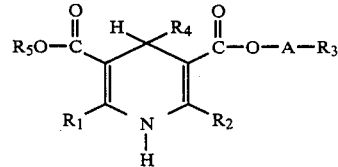

$R_1$ and $R_2$ are each independently selected from the group consisting of lower alkyl, N-alkylphthalimido and derivatives of N-alkylphthalimido, wherein said N-alkyl group comprises at least 2 carbon atoms;

A is a straight or branched chain hydrocarbon moiety containing from 1 to 12 carbon atoms and from 0 to 2 double bonds;

$R_3$ is selected from the group of radicals consisting of hydrogen, $-NH_2$ and $-NCS$;

$R_4$ is an aryl or heteroaryl radical; and $R_5$ is a lower alkyl radical or $A-R_3$; provided that when $R_3$ is a hydrogen radical at least one of $R_1$ and $R_2$ is not lower alkyl, including both pure enantiomers as well as mixtures thereof; and pharmaceutically-acceptable salts thereof.

7 Claims, No Drawings

1,4-DIHYDROPYRIDINES

BACKGROUND OF THE INVENTION

This invention is concerned with certain 1,4-dihydropyridines, their preparation, pharmaceutical compositions containing them and their use as therapeutic agents, particularly as anti-ischaemic and antihypertensive agents.

The compounds of the invention delay or prevent the cardiac contracture which is believed to be caused by an accumulation of intracellular calcium under ischaemic conditions. Calcium overload, during ischaemia, can have a number of additional adverse effects which would further compromise the ischaemic myocardium. These include less efficient use of oxygen for ATP production, activation of mitochondrial fatty acid oxidation, and possibly, promotion of cell necrosis. Thus, the compounds are useful in the treatment or prevention of cardiac conditions, such as angina pectoris, cardiac arrythmias, heart attacks and cardiac hypertrophy. The compounds also process vasodilator activity and are thus useful as antihypertensives and for the treatment of coronary vasospasm.

The structure and presumed mode of action of the 1,4-dihydropyridine calcium antagonists have been reviewed recently in the literature, see Meyer et al., Annual Reports in Medicinal Chemistry, 1983, Chapter 9 and Janis et al., J. Med. Chem 26, 775 (1983). One of the earliest compounds discovered, and still a standard against which new compounds are measured, is nifedipine (U.S. Pat. No. 3,485,847 to Bossert), in which the 2 and 6 positions are substituted by methyl groups, the 4 position by 2-nitrophenyl and the 3 and 5 positions by carboxylic acid methyl ester groups. Similar compounds are disclosed in U.S. Pat. Nos. 3,455,945; 3,325,505; and 3,441,468 to Loev and 3,470,297 and 3,511,837 to Bossert, which introduced variations in the 4-substituent. U.S Pat. Nos. 3,905,970 to Bossert et al., and 3,985,758 to Marakami et al., introduced certain mono- or dialkylamino-alkylene and nitrogen-containing heterocyclic alkylene groups into one or both of the 3,5 ester groups. U.S. Pat. Nos. 4,307,103 and 4,393,070 to Sato disclose 1,4-dihydropyridines in which the 2 position is not subtituted by alkyl, but instead is substituted with cyano, formyl or certain other substituents and the ester group in the 3 position may contain various substituted alkyl groups including substituted alkylaminoalkyl, heterocyclic aminoalkyl and aroylaminoalkyl, including phthalimidoethyl. U.S. Pat. No. 4,448,964 to Muto et al, discloses compounds in which the 3-position ester group contains certain substituted piperidinyl alkylene groups.

It is recognized that useful 1,4-dihydropyridines have a wide variety of structures; however, the nedd for superior activity and specificity remains, and the effect of any particular structural modification on the properties of the compound is generally unpredictable. This is particularly true of modifications in the esters at the 3 and 5 positions, and of modifications at the 2 and 6 positions.

SUMMARY OF THE INVENTION

According to the invention, there are provided novel compounds of the formula:

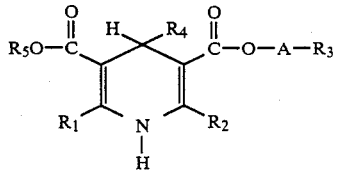

wherein $R_1$ and $R_2$ are independently selected from the group consisting of lower alkyl, N-alkylphthalimido and derivatives of N-alkylphthalimido, wherein said N-alkyl group comprises at least 2 carbon atoms;

A is a straight or branched chain hydrocarbon moiety containing from 1 to 12 carbon atoms and from 0 to 2 double bonds;

$R_3$ is selected from the group of radicals consisting of hydrogen, $-NH_2$ and $-NCS$;

$R_4$ is an aryl or heteroaryl radical; and $R_5$ is a lower alkyl radical or $A-R_3$; provided that when $R_3$ is a hydrogen radical;

at least one of $R_1$ and $R_2$ is not lower alkyl; and pharmaceutically-acceptable salts thereof.

Preferably, A is a radical represented by the general formula

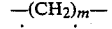

wherein m is an integer of 1 to 12.

$R_4$ is preferably a 3-nitrophenyl, 3-methylphenyl or a 3-trifluoromethylphenyl, radical.

In one preferred embodiment of the instant invention at least one of the radicals represented by $R_1$ and $R_2$ are represented by the general formula

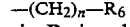

wherein $R_6$ is selected from the group consisting of:

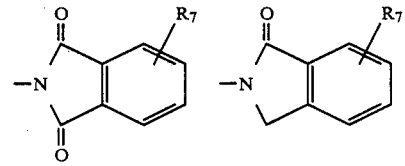

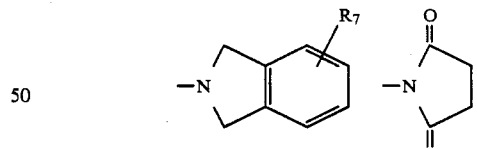

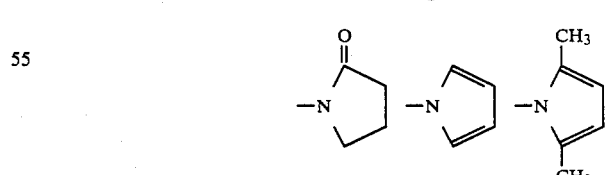

wherein $R_7$ is hydrogen, nitro, cyano, azido, amino, trifluoromethyl, alkylamino, dialkylamino, halo, carboxyl, carbalkoxy, alkyl, alkenyl, alkynyl, cycloalkyl, acylamino, carboxamido, sulfonamido, and $SO_o$-(lower alkyl); wherein n is an integer of from 2 to 12, and o is an integer from 0 to 2. More preferably, n is 2 and $R_6$ is phthalimido. In another preferred embodiment of the instant invention, $R_3$ is selected from the group consisting of radicals represented by the formulae —$NH_2$ and —NCS. In this embodiment, $R_1$, $R_2$ and $R_5$ are preferably methyl radicals and m is preferably 2, 3, 6 or 8.

In particular, the present invention provides the following novel compounds:

1,4-Dihydro-2,6-dimethyl-4-(3-nitrophenyl)-3,5-pyridine dicarboxylic acid, 3-(6-aminohexyl)-5-methyl ester.

1,4-Dihydro-2,6-dimethyl-4-(3-nitrophenyl)-3,5-pyridine dicarboxylic acid, 3-(3-aminopropyl)-5-methyl ester.

1,4-Dihydro-2,6-dimethyl-4-(3-nitrophenyl)-3,5-pyridine dicarboxylic acid, 3-(2-aminoethyl)-5-methyl ester.

1,4-Dihydro-2,6-dimethyl-4-(3-nitrophenyl)-3,5-pyridine dicarboxylic acid, 3-(6-isothiocyanatohexyl)-5-methyl ester.

1,4-Dihydro-2,6-dimethyl-4-(3-nitrophenyl)-3,5-pyridine dicarboxylic acid, 3-(3-isothiocyanatopropyl)-5-methyl ester.

1,4-Dihydro-2,6-dimethyl-4-(3-nitrophenyl)-3,5-pyridine dicarboxylic acid, 3-(2-isothiocyanatoethyl)-5-methyl ester.

1,4-Dihydro-6-methyl-4-(3-nitrophenyl)-2-(2-phthalimidoethyl)-3,5-pyridine dicarboxylic acid, 3-ethyl 5-methyl ester.

1,4-Dihydro-4-(3-nitrophenyl)-2,6-(2-phthalimidoethyl)-3,5-pyridine dicarboxylic acid, diethyl ester.

1,4-Dihydro-2,6-dimethyl-4-(3-methylphenyl)-3,5-pyridine dicarboxylic acid, 5-methyl-3-(6-phthalimido hex-4-enyl) ester.

1,4-Dihydro-2,6-dimethyl-4-(3-methylphenyl)-3,5-pyridine dicarboxylic acid, 3-(6-aminohex-4-enyl)-5-methyl ester.

1,4-Dihydro-2,6-dimethyl-4(3-methylphenyl)-3,5-pyridine dicarboxylic acid, 3-(6-amino[4,5-$^3H_2$]hexyl)-5-methyl ester.

1,4-Dihydro-2,6-dimethyl-4-(3-methylphenyl)-3,5-pyridine dicarboxylic acid, 3-(2-aminoethyl)-5-methyl ester.

1,4-Dihydro-2,6-dimethyl-4-(3-methylphenyl)-3,5-pyridine dicarboxylic acid, 3-(6-aminohexyl)-5-methyl ester.

1,4-Dihydro-2,6-dimethyl-4-(3-methylphenyl)-3,5-pyridine dicarboxylic acid, 3-(2-isothiocyanatoethyl)-5-methyl ester.

1,4-Dihydro-2,6-dimethyl-4-(3-methylphenyl)-3,5-pyridine dicarboxylic acid, 3-(6-isothiocyanatohexyl)-5-methyl ester.

These compounds are useful in the treatment of coronary insufficiency, angina pectoris and hypertension.

The invention also provides pharmaceutical compositions containing the above novel compounds and a pharmaceutically acceptable carrier. Preferably these compositions are in dosage form comprising a clinically effective amount of the active compound.

The invention further provides a method of antagonizing the utilization of calcium in the body of a human being or animal and of treating the above disorders.

In another embodiment of the invention there is provided a method for preparing the novel compounds.

It will be appreciated that certain compounds of the invention are chiral due to their different ester functions. Accordingly, the invention embraces the pure enantiomers as well as mixtures thereof.

Pharmaceutically acceptable salts of the compounds of the formula are prepared in the conventional manner. Acid addition salts are derived from a therapeutically acceptable acid such as hydrochloric acid, hydrobromic acid, acetic acid, propionic acid and, more preferably, from a di- or poly-basic acid such as phosphoric acid, succinic acid, fumaric acid, citric acid, glutaric acid, citraconic acid, glutaconic acid, tartaric acid, maleic acid or ascorbic acid.

A preferred embodiment of this invention is a method of treatment which comprises administering a therapeutically effective amount of a compound of the above formula. In general the daily dose can be from 0.01 mg/kg to 10 mg/kg per day and preferably from 0.2 mg/kg to 4 mg/kg per day, bearing in mind, of course, that in selecting the appropriate dosage in any specific case, consideration must be given to the patient's weight, general health, metabolism, age and other factors which influence response to the drug. The parenteral dosage will be approximately an order of magnitude lower than the oral dosage. Because the activities of the compounds vary somewhat, the effective dosages will also vary.

In another embodiment of this invention there are provided pharmaceutical compositions in dosage unit form which comprise from about 1 mg to about 150 mg of a compound of the above formula, and preferably from about 5 mg to about 100 mg.

The pharmaceutical composition may be in any form suitable for oral use, such as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents elected from the group consisting of sweetening agents, flavoring agents, coloring agents, and preserving agents in order to provide a pharmaceutically elegant and palatable preparation. Tablets may contain the active ingredient in admixture with non-toxic pharmaceutically acceptable excipients which are suitable for manufacture of tablets. These excipients may be inert diluents, for example calcium carbonate, sodium carbonate, lactose, calcium phosphate; granulating and disintegrating agents, such as corn starch, gelatine or acacia; and lubricating agents, such as magnesium stearate, stearic acid or talc. The tablets may be uncoated or they may be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaoline, or as soft gelative capsules wherein the active ingredient is mixed with an oil medium, for example, arachis oil, liquid paraffin or olive oil.

The present invention also embraces aqueous suspensions containing the active compound in admixture with suitable pharmacologically-accepted excipients. Such excipients include suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally-occurring phosphatide, for example lecithin, or a condensation product of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol, for example polyoxyethylene sorbitol monooleate, or condensation product of ethylene oxide with partial esters derived from fatty acids and hexitol anhydrides, for example polyoxyethylene sorbitan monooleate. The aqueous suspensions may also contain one or more preservatives, for example ethyl, or n-propyl-p-hydroxybenzoate, one or more coloring agents, one or more flavoring agents, and one or more sweetening agents, such as sucrose, saccharin, aspartame, mannitol, sorbitol, or sodium or calcium cyclamate.

Dispersable powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative, and flavoring and coloring agents.

The pharmaceutical compositions may also be in the form of a sterile injectable preparation, for example as a sterile injectable aqueous suspension. This suspension may be formulated in a conventional manner using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form for humans will generally contain between about 1 mg and 100 mg of the active ingredient of the formula set forth above.

From the foregoing formulation discussion it should be apparent that the compositions of this invention can be administered orally or parenterally. The term parenteral as used herein includes subcutaneous injection, intravenous, intramuscular, or intrasternal injection or infusion techniques.

The compounds of the present invention may also be administered transdermally with the use of an appropriate transdermal vehicle. The preferred vehicle is 1-n-dodecylazacycloheptan-2-one, as disclosed in U.S Pat. No. 4,405,616.

This invention also includes a method for treating coronary insufficiency (poor circulation, due to cardiac hypertrophy or to other causes), hypertension, angina pectoris, cardiac arrythmia, heart attack, or coronary vasospasm by administering an effective amount of a compound of the present invention. The invention also compounds a method for effecting calcium channel antagonist activity in a mammal, such as a human, by administering an effective amount of a compound represented by the above formula.

The compounds represented by the formula above, may be prepared by the methods used in the Examples, below:

The invention is further illustrated by the following examples which are illustrative of various aspects of the invention, and are not intended as limiting the scope of the invention as defined by the appended claims.

EXAMPLE 1

(a) Preparation of 1-Phthalimidomethyl acetoacetate

A solution of 10.0 g (0.056 mol) of N-(hydroxymethyl)phthalimide and 8.02 g (0.056 mol) of 2,2,6-trimethyl-1,3-dioxen-4-one in 100 ml of toluene was refluxed for 24 hours under nitrogen. Recrystallization in ethyl acetate gives 14.3 g (97%) of an off-white solid: mp 106°–109° C.; NMR (CDCl$_3$) 7.6 (4H,m), 5.6 (2H,s), 3.4 (2H,s), 2.18 (3H,s);

(b) Preparation of 1,4-Dihydro-2,6-dimethyl-4-(3-nitrophenyl-3,5-pyridine dicarboxylic acid, 5-methyl-3-phthalimidomethyl ester A solution of 4.0 g (0.015 mol) of 1-phthalimidomethylacetoacetate, 1.76 g (0.015 mol) of methyl 3-aminocrotonate, and 2.31 g (0.015 mol) of m-nitrobenzaldehyde in 50 ml of isopropanol was refluxed overnight under N$_2$. The yellow solid formed was filtered, washed with ethyl acetate, and dried in vacuo. Recrystallization in ethyl acetate gives 4.38 g (59%) of a yellow powder: mp 248°–252° C.; NMR (CDCl$_3$) 7.6 (9H,m), 5.5 (2H,m), 4.84 (1H,s), 3.48 (3H,s), 2.3 (6H,s).

(c) Preparation of 1,4-Dihydro-2,6-dimethyl-4-(3-nitrophenyl)-3,5-pyridine dicarboxylic acid, 3-aminomethyl-5-methyl ester To a solution of (3.15 mol) of 1,4-dihydro-2,6-dimethyl-4-(3-nitrophenyl)-3,5-pyridine dicarboxylic acid, 5-methyl-3-phthalimidomethyl ester in chloroform/methanol (1:2 V/V) is added 0.9 ml (12.6 mmol) of 40% aqueous methylamine and the mixture is stirred at ambient temperature for 24 hours. The solvent is removed in vacuo and the residue is subjected to flash chromatography (silica gel/ethyl acetate) to yield a pale yellow hygroscopic solid.

Example 2

Preparation of 1,4-Dihydro-2,6-dimethyl-4-(3-methylphenyl)-3,5-pyridine dicarboxylic acid, 3-(2-aminoethyl)-5-methyl ester To a solution of 1,4-dihydro-2,6-dimethyl-4-(3-methyl phenyl)-3,5-pyridine dicarboxylic acid, 5-methyl-3-(2-phthalimidoethyl) ester in chloroform/methanol (1:2 V/V) was added 0.9 ml (12.6 mmol) of 40% aqueous methylamine and the mixture was stirred at ambient temperature for 24 hours. The solvent was removed in vacuo and the residue was subjected to flash chromatography (silica gel/ethyl acetate) to yield 400 mg (38%) of a pale yellow hygroscopic solid: NMR (CDCl$_3$) 6.9 (4H,m), 6.0 (1H,bs), 4.7 (1H,s), 3.9 (2H,q), 3.5 (3H,s), 2.6 (2H,t), 2.3 (3H,s), 2.2 (6H,s), 1.5 (2H,s). Anal. Calcd. C$_{19}$H$_{24}$N$_2$O$_4$: C,66.26; H, 7.02; N, 8.13. Found: C,66.10; H,7.23; N,7.89.

EXAMPLE 3

Preparation of 1,4-Dihydro-2,6-dimethyl-4-(3-nitrophenyl)-3,5-pyridine dicarboxylic acid, 3-(2-aminoethyl)-5-methyl ester To a solution of 0.5 g (0.99 mmol) of 1,4-dihydro-2,6-dimethyl-4-(3-nitrophenyl)-3,5-pyridine dicarboxylic acid, 5-methyl-3-(2-phthalimidoethyl) ester in chloroform/methanol (1:1 V/V) was added 0.34 ml (3.96 mmol) of 40% aqueous methylamine and the mixture was stirred at ambient temperature for 24 hours. The solvent was removed in vacuo and the residue was purified by thin layer chromatography on silica gel using 1:1 V/V ethyl acetate/methanol to give 150 mg (31%) of a pale yellow hygroscopic solid: mp 152°–154° C.; NMR (CDCl$_3$) 7.9–7.1 (4H,m), 6.5 (1H,s), 5.0 (1H,s), 4.0 (2H,t), 3.6 (3H,s), 2.9 (2H,t), 2.35 (6H,s) 1.3 (2H,s).

EXAMPLE 4

Preparation of
1,4-Dihydro-2,6-dimethyl-4-(3-nitrophenyl)-3,5-pyridine dicarboxylic acid, 3-(3-aminopropyl)-5-methyl ester To a solution of 1.0 g (1.92 mmol) of 1,4-dihydro-2,6-dimethyl-4-(3-nitrophenyl)-3,5-pyridine dicarboxylic acid, 5-methyl-3-(3-phthalimidopropyl) ester was added 0.663 ml (7.7 mmol) of 40% aqueous methylamine in chloroform/methanol (1:1 V/V) and the mixture was stirred at room temperature for 48 hours. The solvent was removed in vacuo and the residue was subjected to flash chromatography on silica gel using a 1:1 V/V ethyl acetate/methanol to give 0.46 g (62%) of a yellow oil: NMR (CDCl$_3$) 7.45 (5H,m), 4.95 (1H,s), 4.0 (2H,t), 3.51 (3H,s), 2.55 (2H,m), 2.29 (6H,s), 1.6 (4H,m).

EXAMPLE 5

Preparation of
1,4-Dihydro-2,6-dimethyl-4-(3-methylphenyl)-3,5-pyridine dicarboxylic acid, 3-(6-aminohexyl)-5-methyl ester To a solution of 350 mg (0.66mmol) of 1,4-dihydro-2,6- dimethyl-4-(3-methylphenyl)-3,5-pyridine dicarboxylic acid-5-methyl-3-(6-phthalimidohexyl) ester was added 0.68 ml (7.9 mmol) of 40% aqueous methylamine and the mixture was stirred at ambient temperature for 5 days. The solvent was removed in vacuo and upon acid/base extraction of the residue a yield of 140 mg (55%) of a pale yellow solid was obtained: mp 133°–139° C.; NMR (CDCl$_3$) 6.9 (4H,m), 6.4 (1H,s), 4.8 (1H,s), 3.9 (2H,t), 3.6 (3H,s), 2.6 (2H,m), 2.2 (9H,s), 1.4 (10H,m).

EXAMPLE 6

Preparation of
1,4-Dihydro-2,6-dimethyl-4-(3-nitrophenyl)-3,5pyridine dicarboxylic acid, 3-(6-aminohexyl)-5-methyl ester To a solution of 1.43 g (2.55 mmol) of 1,4-dihydro-2,6-dimethyl-4-(3-nitrophenyl)-3,5-pyridine dicarboxylic acid, 5-methyl-3-(6-phthalimidohexyl) ester was added 0.88 ml (7.1 mmol) of 40% aqueous methylamine in chloroform/methanol (1:1 V/V) and the mixture was stirred at room temperature for 48 hours. The solvent was removed in vacuo, and the residue was subjected to flash chromatography on silica gel using ethyl acetate/methanol (1:1 V/V) to give a yellow oil. Recrystallization from diethyl ether and chloroform gave 0.72 g (66%) of the product: mp 141°–143° C.; NMR (CDCl$_3$) 7.5 (5H,m), 4.98 (1H,s), 3.94 (2H,t), 5.7 (3H,s), 2.63 (2H,m), 2.32 (6H,s), 1.4 (10H,m).

The "deblocking" of the phthalimido derivatives (to yield the corresponding amine) by reaction with a primary alkyl amine, preferably an alkylamine having up to 5 carbon atoms, e.g. methylamine or ethylamine, was effected without reaction of the ester group in the 5-position of the 1,4-dihydropyridine ring. This is in contrast to "deblocking" of similar phthalimido derivatives with reactants such as hydrazine.

EXAMPLE 7

Preparation of
1,4-Dihydro-2,6-dimethyl-4-(3-nitrophenyl)-3,5-pyridine dicarboxylic acid, 3-(2isothiocyanatoethyl)-5-methyl ester A solution of 183.2 mg (0.488 mmol) of 1,4-dihydro-2,6- dimethyl-4-(3-nitrophenyl)-3,5-pyridine dicarboxylic acid, 3-(2-aminoethyl)-5-methyl ester in chloroform, 239 mg (2.84 mmol) of sodium bicarbonate in water, and 65 microliter (0.855 mmol) of thiophosgene was vigorously stirred for 1 hour at room temperature. The chloroform phase was washed with water, dried over magnesium sulfate, filtered, and concentrated in vacuo. The residue was purified by thin layer chromatography on silica gel using 8:2 V/V chloroform/ethyl acetate to yield a yellow hydroscopic solid: mp 162°–164° C.; Anal. Calcd. for $C_{19}H_{19}N_3O_6S$: C, 54.67; H, 4.59; N, 10.07. Found: C,54.46; H, 4.80; N,9.96.

EXAMPLE 8

Preparation of
1,4-Dihydro-2.6-dimethyl-4-(3-nitrophenyl)-3,5-pyridine dicarboxylic acid, 3-(3-isothiocyanatopropyl)-5-methyl ester A solution of 227 mg (0.583 mmol) of 1,4-dihydro-2,6-dimethyl-4-(3-nitrophenyl)-3,5-pyridine dicarboxylic acid, 3-(3-aminopropyl)-5-methyl ester in chloroform, 0.263 mg (3.13 mmol) of sodium bicarbonate in water, and 78 microliters (1.02 mmol) of thiophosgene was vigorously stirred for 1 hour at room temmperature. The chloroform phase was washed with water, dried over magnesium sulfate, filtered, and concentrated in vacuo. The residue was purified by thin layer chromatography on silica gel using 8:2 V/V chloroform/ethyl acetate to yield a yellow, hygroscopic solid: mp 154°–155° C.; Anal. Calcd. for $C_{20}H_{21}N_3O_6S$: C,55.68; H,4.91; N,9.74. Found: C,55.81; H,5.13; N, 9.46.

EXAMPLE 9

Preparation of
1,4-Dihydro-2,6-dimethyl-4-(3-nitrophenyl)-3,5-pyridine dicarboxylic acid, 3-(6-isothiocyanatohexyl)-5-methyl ester A solution of 182.6 mg (0.423 mmol) of 1,4-dihydro-2,6-dimethyl-4-(3-nitrophenyl)-3,5-pyridine dicarboxylic acid, 3-(6-aminohexyl)-5-methyl ester in chloroform, 207 mg (2.45 mmol) of sodium bicarbonate in water, and 57 microliters (0.741 mmol) of thiophosgene was vigorously stirred for 1 hour at room temperature. The chloroform phase was washed with water, dried over magnesium sulfate, filtered, and concentrated in vacuo. The residue was purified by thin layer chromatography on silica gel using 8:2 V/V chloroform/ethyl acetate to yield a yellow, hygroscopic solid: mp 67°–68° C.; Anal. Calcd. for $C_{23}H_{27}N_3O_6S$; C,58.34; H, 5.75; N,8.87. Found: C,58.13; H,6.00; N,8.71.

EXAMPLE 10 (a) Preparation of 4-Tetrahydropyranyloxy-1-butanol

A solution of 11.72 g (0.13 mol) of 1,4-butanediol, 10.0 g (0.12 mol) of dihydropyran and 10 mg of p-toluene sulfonic acid in tetrahydropyran was stirred under nitrogen for 24 hours. Pyridine was added, and the solvent was removed in vacuo. The residue was subjected to flash chromatography (silica gel; petroleum ether/ethyl acetate 3:2 V/V) to give 9.64 g (43%) of a clear oil: NMR (CDCl$_3$) 4.45(1H,s), 3.52(6H,m), 2.68(1H,m), 1.6(10H,m).

(b) Preparation of 4-Tetrahydropyranyloxy-1-butanal

A solution of 10.7 g (62 mmol) of 4-tetrahydropyranyloxy-1-butanal in dichloromethane was added to 34.7 g (92 mmol) of pyridinium dichromate in dichloromethane and stirred for 24 hours at ambient temperature. Petroleum ether/diethyl ether (1:1 V/V) was added, and the mixture was filtered. The filtrate was concentrated in vacuo and the residue distilled to give 3.23 g of a clear oil: bp 58°–60° C./0.5 mm Hg; NMR (CDCl$_3$) 9.5(1H,s), 4.4(1H,s), 3.45(4H,m),2.41 (2H,m), 1.53(8H,m).

(c) Preparation of 2-(Phthalimidoethyl)-triphenyl phosphonium bromide according to a method of Olsen et al., JOC 45 4049 (1980)

A solution of 11.11 g (44 mmol) of 2-bromoethyl phthalimide and 11.47 g (44 mmol) of triphenylphosphine in xylene was refluxed for 36 hours. The mixture was cooled, filtered, washed with diethyl ether, and dried to yield 12.5 g of a white solid: mp 246°–247° C.; NMR (CDCl$_3$) 7.5 (19H,m), 4.34 (4H,m).

(d) Preparation of 1-Phthalimido-6-tetrahydropyranyloxy-2-hexene

To a solution of 1.5 g (2.9 mmol) of 2-(phthalimidoethyl) triphenylphosphonium bromide and 325 mg (2.9 mmol) of potassium tert-butoxide in tetrahydropyran was added 0.5 g (2.9 mol) of 4-tetrahydropyranyloxy-1-butanal. The mixture was refluxed for 17 hours, filtered, and the solvent was removed in vacuo. The residue was dissolved in ethyl acetate, washed with water, the organic phase dried, concentrated in vacuo, and the residue subjected to flash chromatography (silica gel; petroleum ether/ethyl acetate 9:1 V/V) to give 0.11 g of a yellow oil: NMR (CDCl$_3$) 7.53 (4H,m), 5.38 (2H,m), 4.48 (1H,s), 4.2 (2H,d), 3.5 (4H,m), 2.24 (2H,m), 1.54 (8H,m).

(e) Preparation of 1,4-Dihydro-2,6-dimethyl-4-(3-methyl phenyl)-3,5-pyridine dicarboxylic acid, 5-methyl-3-(6-phthalimidohex-4-enyl) ester A solution of 1.8 g (5.7 mmol) of 1-phthalimido-6-tetrahydropyranyloxy-2-hexene, 2.67 g (8.1 mmol) of 1,4-dihydro-2,6-dimethyl-4-(3-methylphenyl)-3,5-pyridine dicarboxylic acid, dimethyl ester and 10 mg of p-toluene sulfonic acid in toluene was refluxed under nitrogen for 72 hours. The solvent was removed in vacuo, and the residue was subjected to flash chromatography (silica gel; petroleum ether/diethyl ether 3:2 V/V) to give 0.69 g of a yellow, hygroscopic solid: NMR (CDCl$_3$) 7.57(4H,m), 6.9(4H,m), 6.12(1H,s), 5.35(2H,m), 4.85(1H,s), 4.05(4H,m), 3.56(3H,s), 1.6–2.4(13H,m).

(f) Preparation of 1,4-Dihydro-2,6-dimethyl-4-(3-methylphenyl)-3,5-pyridine dicarboxylic acid, 3-(6-aminohex-4-enyl)-5-methyl ester A solution of 0.69 g (1.3 mmol) of 1,4-Dihydro-2,6-dimethyl-4-(3-methylphenyl)-3,5-pyridine dicarboxylic acid, 5-methyl-3-(6-phthalimidohex-4-enyl) ester and 1.2 ml (14 mmol) of 40% aqueous methylamine in chloroform/methanol (1:1) V/V was stirred at ambient temperature for 48 hours. The solvent was removed in vacuo and upon acid/base extraction of the residue, 0.23 g of product was obtained as a yellow oil: NMR (CDCl$_3$) 6.85(4H,m), 64(1H,s), 4.85(1H,s), 3.9(2H,t), 3.52(3H,s), 3.1(2H,m), 2.2–1.3(15H,m). Anal. Calcd. for $C_{23}H_{30}N_2O_4$: C, 69.32; H, 7.59; N, 7.03. Found: C, 69.43; H, 7.60; N, 7.13.

EXAMPLE 11

Preparation of 1,4-Dihydro-2,6-dimethyl-4(3-methylphenyl)-3,5-pyridine dicarboxylic acid, 3-(6-amino[4,5-$^3$H$_2$]hexyl)-5-methyl ester Tritiation of the 4-hexenyl double bond was performed by the National Tritiation Facility, Berkeley, CA. To a solution of 85 mg (0.21 mmol) of 1,4-dihydro-2,6-dimethyl-4-(3-methylphenyl)-3,5-pyridine dicarboxylic acid, 3-(6-aminohex-4-enyl)-5-methyl ester in tetrahydrofuran was added 30 mg of 10% Pd/C and 2 drops of [$^3$H]acetic acid. This mixture was subjected to hydrogenation using tritium gas. After removal of the excess tritium, catalyst, and solvent, the residue was treated with thiophosgene as described in the preparation of 1,4-dihydro-2,6-dimethyl 4(3-methylphenyl)-3,5-pyridine dicarboxylic acid, 3-(6-isothiocyanatohexyl)-5-methyl ester, above. The tritiated NCS derivative was identified by comparison with the untritiated material, which has virtually the same physical and spectral characteristics.

EXAMPLE 12

(a) Preparation of N-Phthalylalanine

A mixture of 89.09 g (1.0 mol) of β-alanine and 148.12 g (1.0 mol) of phthallic anhydride was stirred at 180°–190° C. for 30 minutes. Upon adding water, a solid formed which was filtered, washed with water, and recrystallized in ethanol/water to give 178.0 g of a white powder: mp 152°–153° C.; NMR (CDCl$_3$) 7.8 (4H,s), 4.0 (2H,t), 2.7 (2H,t).

(b) Preparation of (3-Phthalimido)propionyl chloride 87.6 g (0.4 mol) of N-phthalylalanine was added to a stirring suspension of 83.2 g (0.4 g mol) of phosphorus pentachloride in toluene at 60° C. under nitrogen. After the mixture was stirred for 2 hours, the solvent and excess phosphorus pentachloride were removed to give a white solid Recrystallization in benzene/petroleum ether yielded 76.0 g of a hygroscopic white powder: mp 94°–99° C.; NMR (CDCl$_3$) 7.7 (4H,m) 3.9 (2H,t), 3.2 (2H,t).

(c) Preparation of 2-(1-Oxo-3-phthalimidopropyl) diethyllmalonate

A solution of 18.9 g (118 mmol) of diethyl malonate in ethanol was added slowly to a mixture of 2.8 g (118 mmol) of magnesium turnings in ethanol under nitrogen. Upon complete addition, diethyl ether was added and the reaction mixture was refluxed for 3 hours. The solvent was removed in vacuo, the residue dissolved in diethyl ether, and a solution of 28 g (118 mmol) of (3-phthalimido) propionyl chloride in diethyl ether/tetrahydrofuran (3:1) V/V was added to the dissolved residue. After refluxing for 2 hours, 150 ml of 10% H$_2$SO$_4$ (by wt.) was added to the mixture. The organic layer was separated, washed with 10% sodium bicarbonate and water, dried, and the solvent removed to give a viscous oil which crystallized. Recrystallization in dichloromethane/diethyl ether/petroleum ether yielded 32.0 g of a white powder: mp 66°-69° C.; NMR (CDCl$_3$) 7.6 (4H,bs), 4.0 (6H,m), 2.8 (3H,m), 1.2 (6H,m).

(d) Preparation of 3-Oxo-5-Phthalimidopentanoic acid, Ethyl Ester 2-(1-Oxo-3-phthalimidopropyl)diethyl malonate (6.4 g, 180 mmol) was steam distilled for 3 hours. The pot flask was cooled, extracted into dichloromethane, dried, and the solvent removed in vacuo to give a pale yellow solid. Recrystallization in ethanol yielded 40.0 g of a white solid: mp 90°-92° C.; NMR (CDCl$_3$) 7.6 (4H,m), 3.9 (4H,m), 3.4 (2H,s), 2.9 (2H,t), 1.3 (3H,t).

(e) Preparation of 1,4-Dihydro-6-methyl-4(3-nitrophenyl)2-(2-phthalimidoethyl)-3,5-pyridine dicarboxylic acid-3-ethyl-5-methyl ester A solution of 6.0 g (20 mmol) of 3-Oxo-5-phthalimidopentanoic acid, ethyl ester, 3.1 g (20 mmol) of 3-nitrobenzaldehyde, 2.3 g (20 mmol) of methyl 3-aminocrotonate and 2-propanol was refluxed under nitrogen for 20 hours. The solvent was removed in vacuo, and the residue subjected to flash chromatography (silica, 8:1 V/V diethyl ether/petroleum ether) to give a yellow solid. Recrystallization in dichloromethane/diethyl ether/petroleum ether yielded 4.0 g of a yellow solid: mp 136°-138° C.; NMR (CDCl$_3$) 7.5 (8H,m), 6.6 (1H,s), 5.0 (1H,s), 4.0 (2H,q), 3.8 (2H,m), 3.5 (3H,s), 3.0 (2H,q), 2.2 (3H,s), 1.2 (3H,t).

EXAMPLE 13

Preparation of 1,4-Dihydro-4(3-nitrophenyl)-2,6-(2-phthalimidoethyl)-3,5-pyridine dicarboxylic acid, ethyl ester A solution of 5.0 g (17 mmol) of 3-oxo-5phthalimidopentanoic acid, ethyl ester, 1.28 g (9 mmol) of 3-nitrobenzaldehyde, 0.62 ml (9.4 mmol) of concentrated ammonium hydroxide, and ethanol was refluxed for 72 hours under nitrogen. The solvent was removed in vacuo and the residue was subjected to flash chromatography (silica, 8:2 V/V petroleum ether/diethyl ether) to give 2.0 g of a yellow solid: mp 115°-117° C.; NMR (CDCl$_3$) 7.5 (12H,m), 4.9 (1H,s), 3.9 (8H,m), 3.4 (4H,q), 1.2 (6H,t).

Example 14

The activity of the compounds of this invention may be demonstrated by the following binding assay.

The assay was carried out as described by Fairhurst et al., Life Sciences, 32, 1331 (1983). Washed rabbit skeletal muscle membranes (fraction 2-8X) were incubated for 30 minutes at 25° C. in 2 ml final volume of medium containing 12.5 mM HEPES buffer pH 7.4 and $0.5 \times 10^{-9}$M/$^3$H-nitrendipine having a specific activity of approximately 17 Ci/mmol.

Parallel experiments contained, additionally, unlabelled nifedipine at a final concentration of $10^{-6}$M, to give the non-specific binding values.

The incubation tubes were rapidly chilled in ice and the contents filtered through Whatman GF/B filters on a Millipore manifold, and the filters washed with $2 \times 10$ ml ice-cold HEPES buffer. The filters were placed in scintillation counting vials with 8 ml of Cytoscint cocktail, disrupted mechanically by shaking for 30 minutes and counted.

Specific binding was determined by subtracting the radioactivity in the presence of nifedipine from that in the absence. Drugs which interact at the dihydropyridine (DHP) site will reduce this specific binding in a dosedependent manner. The assays for the compounds of this invention were made with logarithmically spaced concentrations, the data were plotted on a probitconcentration plot, and the IC$_{50}$ read off. The K$_I$ of the compound was calculated by standard techniques. The results of the assay were shown in Table I below.

TABLE I

| Ex. No. | R$_1$ | R$_2$ | A-R$_3$ | R$_4$ | R$_5$ | Binding Assay KI (moles) |
|---|---|---|---|---|---|---|
| 2 | CH$_3$ | CH$_3$ | C$_2$H$_4$NH$_2$ | 3-methyl-phenyl | CH$_3$ | $1.25 \times 10^{-6}$ |
| 3 | CH$_3$ | CH$_3$ | C$_2$H$_4$NH$_2$ | 3-nitro-phenyl | CH$_3$ | $>10^{-7}$ |
| 7 | CH$_3$ | CH$_3$ | C$_2$H$_4$NCS | 3-nitro-phenyl | CH$_3$ | $1.3 \times 10^{-9}$ |
| 8 | CH$_3$ | CH$_3$ | C$_3$H$_6$NCS | 3-nitro-phenyl | CH$_3$ | $1.6 \times 10^{-9}$ |
| 9 | CH$_3$ | CH$_3$ | C$_6$H$_{12}$NCS | 3-nitro-phenyl | CH$_3$ | $1.9 \times 10^{-9}$ |
| 12(e) | CH$_3$ | 2-phthalimidoethyl | C$_2$H$_5$ | 3-nitro-phenyl | CH$_3$ | $1.05 \times 10^{-7}$ |
| 13 | 2-phthalimidoethyl | 2-phthalimidoethyl | C$_2$H$_5$ | 3-nitro-phenyl | C$_2$H$_5$ | $1.12 \times 10^{-6}$ |
| 14 | nifedipine | | | | CH$_3$ | $7.6 \times 10^{-9}$ |

While particular embodiments of the invention have been described it will be understood of course that the invention is not limited thereto since many obvious modifications can be made and it is intended to include within this invention any such modifications as will fall within the scope of the appended claims.

What is claimed is:

1. A compound represented by the formula:

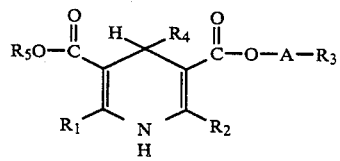

wherein $R_1$ and $R_2$ are each methyl radicals;

A is a radical represented by the formula

—(CH2)m— and m is 2, 3, or 6;

$R_3$ is —NCS;

$R_4$ is selected from the group consisting of 3-nitrophenyl and 3-methylphenyl;

$R_5$ is a methyl radical; including both pure enantiomers as well as mixtures thereof; or a salt thereof.

2. A compound according to claim 1 wherein $R_4$ is 3-nitrophenyl and m is 2.

3. A compound according to claim 1 wherein m is 3 and $R_4$ is 3-nitrophenyl.

4. A compound according to claim 1 wherein $R_4$ is 3-nitrophenyl and m is 6.

5. A compound according to claim 1 wherein $R_4$ is 3-methylphenyl and m is 2.

6. A compound according to claim 1 wherein $R_4$ is 3-methylphenyl and m is 6.

7. A method for treating coronary insufficiency, hypertension, angina pectoris, cardiac arrythmia, heart attack, or coronary vasospasm, comprising the step of administering an effective amount of a compound of claim 1 to a patient in need of such treatment.

* * * * *